(12) United States Patent
Rafailov et al.

(10) Patent No.: US 9,304,310 B2
(45) Date of Patent: Apr. 5, 2016

(54) THREE DIMENSIONAL STIMULATED EMISSION DEPLETION MICROSCOPY

(71) Applicant: The University of Dundee, Dundee (GB)

(72) Inventors: Edik U. Rafailov, Dundee (GB); David J. Carnegie, Dundee (GB); Grigorii Sokolovskii, Dundee (GB); Pablo Loza Alvarez, Barcelona (ES); David Artigas, Barcelona (ES)

(73) Assignee: UNIVERSITY OF DUNDEE, Dundee (GB)

( * ) Notice: Subject to any disclaimer, the term of this patent is extended or adjusted under 35 U.S.C. 154(b) by 0 days.

(21) Appl. No.: 14/365,530

(22) PCT Filed: Dec. 14, 2012

(86) PCT No.: PCT/GB2012/000901
§ 371 (c)(1),
(2) Date: Jun. 13, 2014

(87) PCT Pub. No.: WO2013/088106
PCT Pub. Date: Jun. 20, 2013

(65) Prior Publication Data
US 2014/0347723 A1 Nov. 27, 2014

(30) Foreign Application Priority Data

Dec. 14, 2011 (GB) .................................. 1121514.2

(51) Int. Cl.
*G01B 21/16* (2006.01)
*G02B 21/16* (2006.01)
(Continued)

(52) U.S. Cl.
CPC ............ *G02B 21/16* (2013.01); *G01N 21/6458* (2013.01); *G02B 21/0032* (2013.01);
(Continued)

(58) Field of Classification Search
CPC .............................. G01B 21/16; G01N 21/6458
See application file for complete search history.

(56) References Cited

U.S. PATENT DOCUMENTS 8,558,998 B2 * 10/2013 Feldkhun ........... G01N 21/4795
250/351
8,586,945 B2 * 11/2013 Reuss et al. ................ 250/458.1
(Continued)

FOREIGN PATENT DOCUMENTS

WO 2010084317 A1 7/2010
WO 2012049381 A2 4/2012

OTHER PUBLICATIONS

Phelan et al., "Conical diffraction and Bessel beam formation with a high optical quality biaxial crystal", Optics Express, vol. 17, No. 15, Jul. 20, 2009, 9 pages.
(Continued)

*Primary Examiner* — David Porta
*Assistant Examiner* — Faye Boosalis
(74) *Attorney, Agent, or Firm* — Drinker Biddle & Reath LLP

(57) ABSTRACT

A STED microscope for producing a 3D image. The microscope has an excitation laser source for providing an excitation laser beam and a depletion laser source for providing stimulated emission depletion laser beam. The excitation beam is capable of exciting fluorescent markers in a sample placed in the sample region and the depletion beam is capable of inducing stimulated emission in the fluorescent marker in the sample in a region around the excitation beam to restrict the size of the region within which the fluorescent markers are excited and wherein the depletion laser source goes through an optical element which creates a cone refractive pattern which induces stimulated emission in the fluorescent marker in the sample. The shape of the light hollow of the cone refractive pattern varies at different distances from the source. This depth profile can be used to distinguish between positions at varying depths within a sample to create a 3D image. The combination of varying intensity across the sample and at different depths means that the present invention is able to produce images with lateral and axial resolutions ranging from the micro to the nano regime.

14 Claims, 3 Drawing Sheets

(51) Int. Cl.
  *G02B 21/00* (2006.01)
  *G02B 27/58* (2006.01)
  *G01N 21/64* (2006.01)
  *G02B 1/02* (2006.01)
  *G02B 27/09* (2006.01)

(52) U.S. Cl.
  CPC ............ *G02B21/0076* (2013.01); *G02B 27/58* (2013.01); *G01N 2201/06113* (2013.01); *G02B 1/02* (2013.01); *G02B 27/0927* (2013.01)

(56) References Cited

U.S. PATENT DOCUMENTS

2007/0171432 A1  7/2007  Neuhauser et al.
2009/0168613 A1  7/2009  Sirat
2011/0031411 A1* 2/2011  Baer ................. G02B 21/0072
                                            250/459.1

OTHER PUBLICATIONS

Reuss et al., "Birefringent device converts a standard scanning microscope into a STED microscope that also maps molecular orientation", Optics Express, OSA, vol. 18, No. 2, Jan. 18, 2010, 10 pages.
International Search Report for PCT/GB2012/000901, Mar. 21, 2013.
Written Opinion of the International Searching Authority for PCT/GB2012/000901, Mar. 21, 2013.
UK Search Report for GB1121514.2, Apr. 13, 2012.

* cited by examiner

THREE DIMENSIONAL STIMULATED EMISSION DEPLETION MICROSCOPY

The present invention relates to Stimulated Emission Depletion (STED) Microscopy and in particular to providing compact three-dimensional STED microscopes with improved optical characteristics.

BACKGROUND

As optical microscopy allows in vivo imaging, it has become one of the most important tools in biological research and technical advances are continually pushing the limits of microscope performance and versatility. In recent years new approaches have been proved to produce super resolution. Examples of these new strategies include Stimulated Emission Depletion Microscopy (STED), Photo Activation Localization Microscopy (PALM) or Stochastic Optical Reconstruction Microscopy, STORM) and structured illumination.

Super resolution is defined as microscopy which allows imaging at a resolution beyond the diffraction limit of the incident electromagnetic radiation. In STED, the diffraction limit is overcome by producing an effective nanoscale fluorescent spot. This is done by depleting electronic excited states via stimulated emission in the peripheral region of a focused fluorescent spot while leaving a small fluorescent region in the centre intact.

STED was the first concrete and feasible concept which showed that the diffraction limit could be exceeded in fluorescence microscopy. Theoretically proposed in 1996 and experimentally demonstrated in 1999, STED microscopy is based on the reduction in the size of the effective focus by switching off the fluorescence ability of the fluorophores in the outer part of the excitation focus. To accomplish this, two spatial overlaid beams with different wavelength are necessary. The first one, called the excitation beam excites the fluorophore molecules within the light path from the ground state to the first electronically excited stated. The second one, called the depletion beam or STED beam, empties the excited states of the fluorophore through stimulated emission in such a way that the fluorophore is switched off. Importantly, the shape of the focused STED beam may be modified to obtain substantially zero intensity at the centre and high intensities at the periphery. This shape can be created, for example, by applying a vortex phase plate. In this way, after excitation, the depletion beam switches-off all the fluorophores except those at the centre, restricting the effective fluorescence generation to a sub-diffraction-sized volume.

The higher the applied STED intensity, the more efficient the depletion is and thus the smaller the central region where the fluorescence is unaltered. Thus, in diamond colour centres, resolutions as small as 6 nm have been demonstrated. On biological samples, resolutions are typically in the 40 to 90 nm range.

STED relies on several fluorophore parameters such as high cross section for stimulated emission, no excitation at the depletion wavelength and photo-stability at depletion and excitation wavelengths. This means that for the currently available dyes, STED lasers which are able to produce a beam at the appropriate wavelength and having sufficient intensity are required. For example, in the earlier designs, pulse sources such as Ti:sapphire lasers producing high peak powers were used. Under this scheme, the use of STED microscopy was limited to the dyes able to be depleted in the 700 nm region (Pyridine3, RH-41411, Atto647N9, Atto655). In an effort to access other visible fluorescent markers, Ti: sapphire lasers or regenerative amplifiers where combined with frequency-doubled optical parametric oscillators (OPO) (RegA) and optic parametric amplifier (OPA). The use of super continuum laser sources has also allowed STED imaging at different colours.

Other novel light sources based on a comb-like spectrum generated in standard single-mode fibres via stimulated Raman scattering (SRS) have been proposed. These SRS light sources enable multicolour STED from green to red (530 and 616 nm). More recently CW lasers have become available with sufficient power for STED microscopy. CW lasers simplify the STED microscope setup considerably because temporal synchronization of the STED pulses with their excitation counterparts becomes obsolete. Thus, a CW STED system has been recently commercialized using a fibre laser with a wavelength of 592 nm and a power of 1.5 W. Under this configuration super resolution on samples with visible fluorescent dyes (Alexa488, Chromeo488, Atto488, FITC) and fluorescent proteins (eYFP, Citrin, Venus) can be obtained.

Typically STED images can be obtained from planes 10 to 15 μm inside the sample while in confocal microscopy, this can go up to 200 μm. This is because sample aberrations produce distortions of the STED beam compromising the super resolution capability at those the penetration depths.

STED microscopy has been used to demonstrate the concept of super resolution imaging in living samples. For instance, S. cerevisiae yeast cells were one of the first organisms imaged with STED microscopes. Since then more complex organisms and their components have been observed using different STED configurations. These include different cytoskeletal structures (tubulin and vimentin), endoplasmic reticulum, protein clusters on the cell membrane in mammalian cell dendritic structures and synaptic vesicles in movement.

It should be noted that standard STED is an intrinsic 2D super resolution technique. This is achieved only on the transversal plane while the axial resolution is limited to that of a conventional confocal microscope. STED has been shown to produce 3D super resolution images by introducing an extra arm with an additional phase mask that introduces a $\pi$ phase shift in a central disk. However, these phase masks are wavelength dependant and the setup requires the use of two cross polarized beams that have to be combined in an interferometer-based arrangement. This adds complexity and seriously compromises the stability and versatility of the system.

SUMMARY OF THE INVENTION

It is an object of this invention to create an improved STED microscope which makes STED attractive and affordable for super-resolution imaging and which can provide 3D super-resolution.

In accordance with a first aspect of the invention there is provided a STED microscope comprising:

an excitation laser source for providing an excitation laser beam;

a depletion laser source for providing stimulated emission depletion laser beam;

optics for guiding the excitation beam and the depletion beam to a sample region where the excitation beam is capable of exciting fluorescent markers in a sample placed in the sample region and the depletion beam is capable of inducing stimulated emission in the fluorescent marker in the sample in a region around the excitation beam to restrict the size of the region within which the fluorescent markers are excited and wherein the depletion laser source goes through an optical element which creates a cone refractive pattern which induces stimulated emission in the fluorescent marker in the sample.

Advantageously, the present invention provides a STED microscope which can provide 3D STED using a single depletion laser source by using an optical element which creates a cone refractive pattern.

Preferably, the cone refractive pattern has a substantially ovoid shaped light intensity, with light being absent from the ovoid inner volume.

Preferably, the optical element comprises a cone refractive crystal arrangement which creates conical refraction.

Optionally, the optical element comprises a cone refractive crystal arrangement which creates conical refraction at the crystal with a pseudovector.

Preferably, the optical element is a biaxial or birefringent crystal.

Optionally, the biaxial or birefringent crystal cut in the direction which creates the conical refraction phenomenon.

Optionally, the crystal is a rare earth crystal

Optionally, the cone refractive pattern is controllable by varying crystal length.

Optionally, the cone refractive pattern is controllable by varying the crystal material.

Optionally, the cone refractive pattern is controllable by varying the focal length of the input lens.

There variables allow different shapes and sizes of cone refractive pattern intensity distribution to be created.

Preferably, the optical element induces stimulated emission in the fluorescent marker in the sample in a 3D region surrounding one point of the excitation beam.

Preferably, the beam created by the emission laser source and formed using the CR crystal propagates through two or more optical elements to produce controllable hollow 3D light spot.

Preferably, the excitation laser source and the emission laser source operate in the visible region of the electromagnetic spectrum.

BRIEF DESCRIPTION OF THE DRAWING

The present invention will now be described by way of example only with reference to the accompanying drawing in which.

DETAILED DESCRIPTION OF THE DRAWING

Figure 1A:
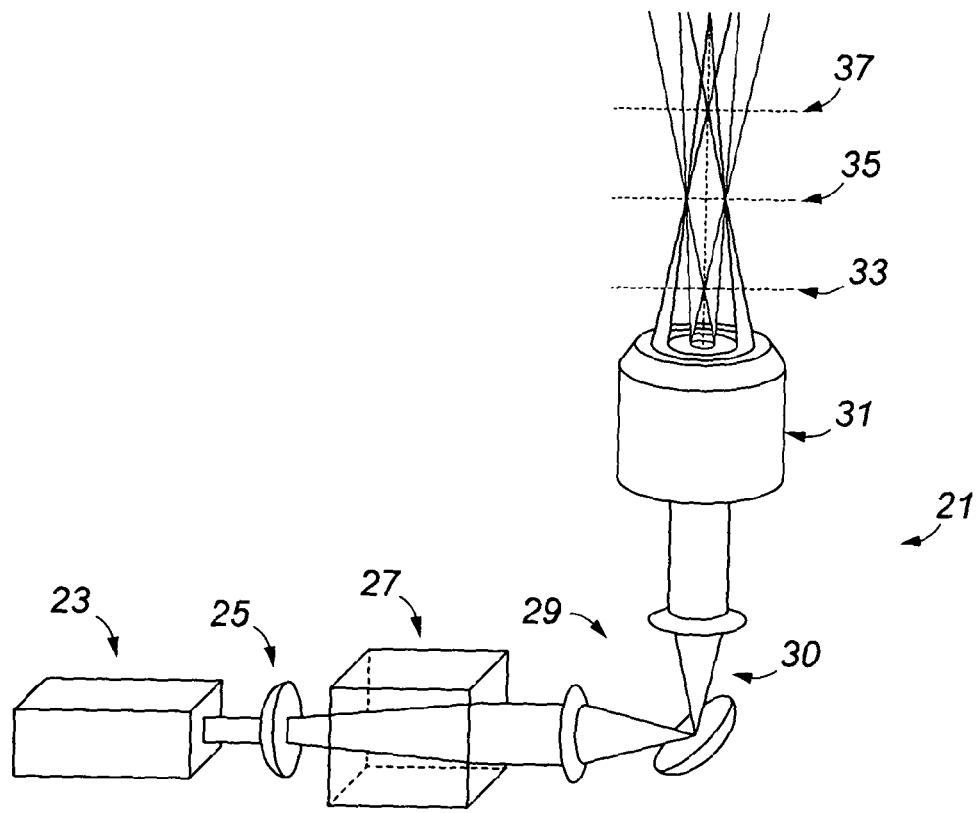
FIG. 1 is a schematic diagram of a system which can produce conical refraction.

The present invention provides a compact, reliable 3D STED imaging that can be provided by a single STED beam.

In Conical Refraction (CR) propagation of a laser light in a biaxial crystal causes the intensity and polarisation distribution of the beam to undergo a unique transformation. Within the crystal the light beam evolves as a hollow cone, and at the exit surface of the crystal, it will refract as a hollow tube. The biaxial crystal is produced in a synthetic crystal which is cut and polished to give a high precision orientation. The conical refraction based optical schemes of the present invention enable formation of a hollow 3D light spot. In one embodiment of the present invention, the Gaussian beam formed using the conical refraction crystal propagates through two and more consecutive CR crystals to produce controllable "hollow" 3D light spot to be used in a STED microscope.

Observation of the CR phenomenon is made using the apparatus as shown in FIG. 21 which comprises a laser 23, a lens 25 and an optically biaxial CR crystal 27 which is cut perpendicular to one of its optic axes. Coupling optics 29 transmits the beam 30 to the objective 31 from where the spatial evolution of an incident Gaussian beam and its transformation under the effect of CR is observed.

Figure 1B:
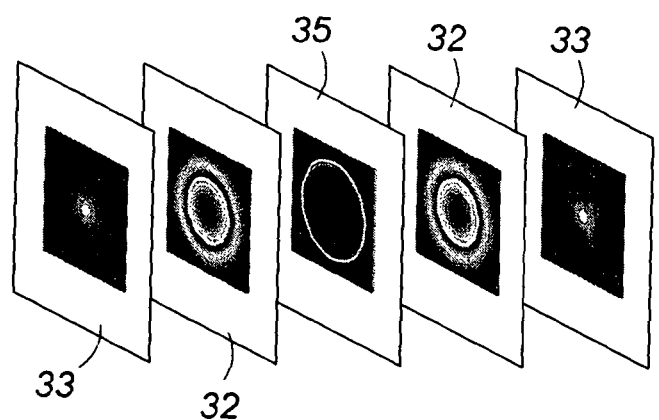

The beam intensity profiles are shown in FIG. 1b. A first Raman spot 33 is observed then the light 35 is observed as a series of rings (Poggendorf) then as a single ring in the Lloyd plane, which is also called the focal image plane. After the Lloyd plane, the beam then progresses to a second series of Poggendorf rings 32 before evolving to an axial spike first noted by Raman7. Finally, the beam returns to the original profile in the far field. The Lloyd plane is also a symmetry plane. The centre of the ring in the Lloyd plane is laterally shifted by an amount, denoted here by C, which depends on the crystal length and a factor representing the crystal's ability for conical refraction. The direction of this lateral shift can be defined as a property of the crystal orientation. The pseudo-vector can also be empirically defined as being perpendicular to both the beam propagation direction and the direction of the lateral shift obeying a right hand rule. Another feature is related to the longitudinal shift of the Lloyd plane. The longitudinal shift is given by $$\Delta = d\left(1 - \frac{1}{n}\right). \quad (1)$$

Here n is the refractive index of the crystal in the propagation direction of the photons.

The spatial evolution of an incident Gaussian beam and its transformation under the effect of CR shows that the ring plane is in fact a symmetry plane. This ring plane is also laterally shifted and it has an offset centre above the optical axis defined by the vector C, whose magnitude-depends upon the length and other properties of the crystal. The distance from the Lloyd plane to each of the Raman spikes (R), called "focal farness" F. This depends on the waist radius of the incident Gaussian beam and the "conicity" parameter of the crystal. Therefore, the size of "light hollow" beam can be controlled by developing appropriated crystals and optimising the focusing lens.

Figure 2A:
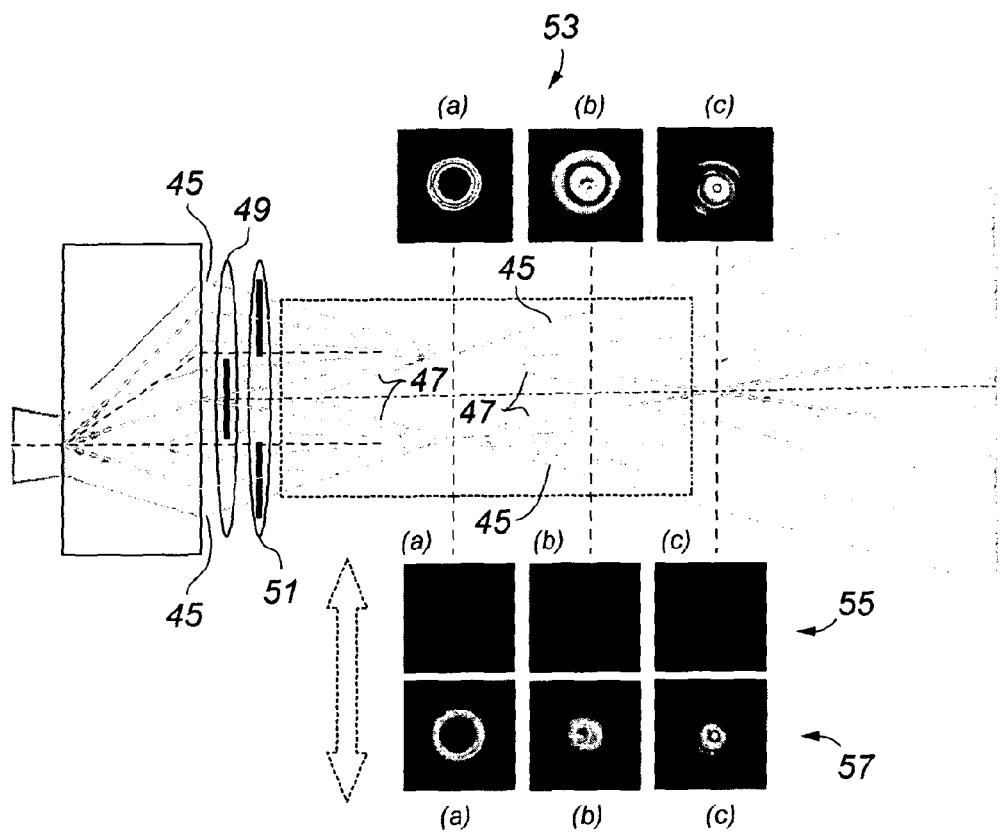
FIG. 2a is a schematic geometrical optics illustration of the conical refraction mechanism along with beam shapes at different points in the evolution of the beam and FIG. 2b shows a side-on intensity profile of a conically refracted beam.

In FIG. 2a, a geometrical optics model of the CR mechanism shows propagation of two cones (47 and 45) after the CR crystal. The path of the individual cones can be easily visualised by blocking the inner or outer part of the CR beam with pin-hole 51 or an opaque spot 49 placed in the first Raman plane. Corresponding intensity distributions for each of the cones in Lloyd, Poggendorff and Raman planes are shown. The undisturbed intensity distributions are shown at reference numeral 53, those for the pin hole at reference numeral 55 and those with the opaque spot at reference numeral 57.

Figure 2B:
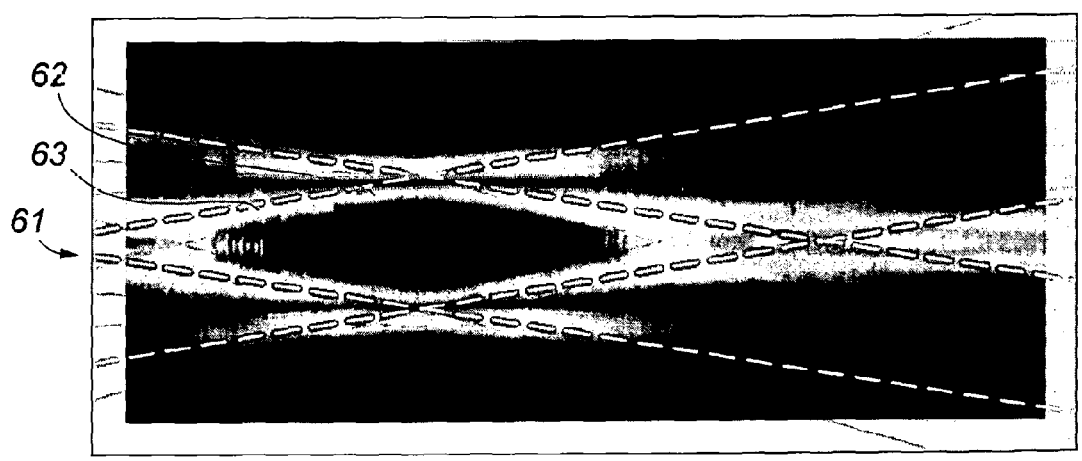

FIG. 2b, shows the side-on intensity profile for the undisturbed beam 61 of a as it evolves through space. This clearly shows that a central dark area surrounded by a generally ovoid shaped light intensity distribution 63. The use of a generally ovoid shaped light intensity is of particular utility in STED microscopy because it provides a change in the light intensity at different depths in a sample. The beam shape may be controlled by careful selection of crystal length and material as well as the focal length of the input lens. This will allow different shapes and sizes of ovoid beam intensity distribution to be created.

Figure 3:
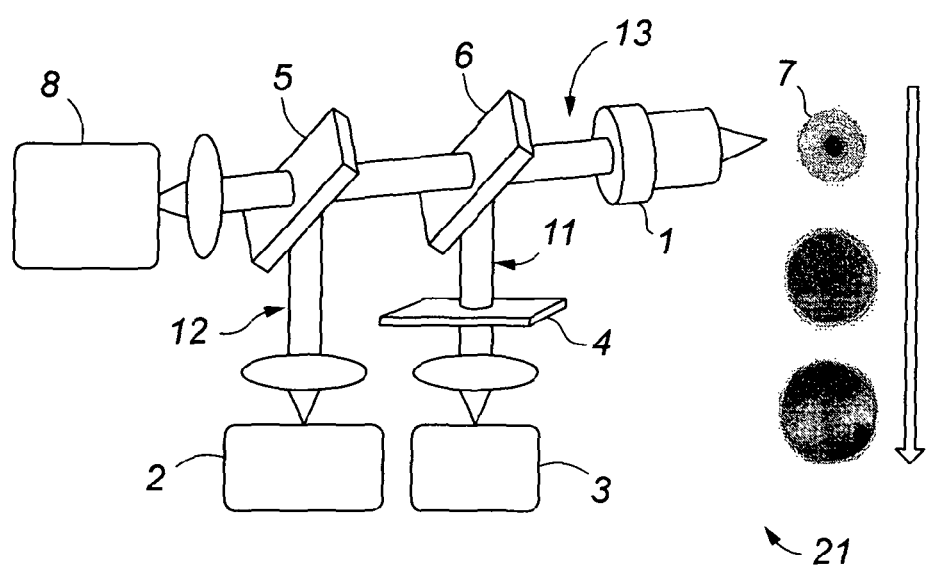
FIG. 3 shows an example of an embodiment of a STED microscope using CR elements.

FIG. 3 is an example of the present invention and comprises a confocal microscope assembly 1 in which the depletion laser source or STED laser comprises a laser source 5 and a conical refraction element 1. The output beam of the laser source 105 passes through the conical refraction element 11 to produce a ring shaped depletion laser beam 13. The excitation laser source 7 generates the excitation laser beam 109 which is reflected at dichroic mirror 15.

The depletion laser beam 13 and the emission laser beam 9 are combined by the dichroic beam combiner 17 to form the illumination-light beam 21 which travels through the microscope optics 19, to the sample plane 21. The light leaving the sample plane 23 travels through the microscope optics 19 via the dichroic beam combiner 17 and the dichroic mirror 15, to the fluorescence detector 23.

As described above, known 3D STED systems produce super resolution images by introducing an extra arm with an additional phase mask that introduces a π phase shift in a central disk. However, these phase masks are wavelength dependant and the setup requires the use of two cross polarized beams that have to be combined in an interferometer-based arrangement. This adds complexity and seriously compromises the stability and versatility of the system.

The present invention provides a 3D light hollow for 3D STED microscopy which is produced using conical refraction without the need of any beam recombination, greatly simplifying the setup. The shape of the light hollow varies at different distances from the source. This depth profile can be used to distinguish between positions at varying depths within a sample to create a 3D image. The combination of varying intensity across the sample and at different depths means that the present invention is able to produce images with lateral and axial resolutions ranging from the micro to the nano regime. Furthermore, on the depletion beam, the same CR crystal can be used for any desirable wavelengths without introducing any modification in the setup. This is special suited for targeting GFP markers, one of the most commonly used biological labels. In addition different combinations of laser wavelengths can be used for allowing "multicolour STED". This will make the technique highly compatible with already available labelling approaches including imaging of living cells in their working environment. We envision that by implementing such a neat approach, STED technique will become much more cost effective, accessible and versatile.

Improvements and modifications may be incorporated herein without deviating from the scope of the invention.

The invention claimed is:

1. A STED microscope for producing a 3D super resolution image, the microscope comprising:
   an excitation laser source for providing an excitation laser beam;
   a depletion laser source for providing stimulated emission depletion laser beam;
   optics for guiding the excitation beam and the depletion beam to a sample region where the excitation beam is capable of exciting fluorescent markers in a sample placed in the sample region and the depletion beam is capable of inducing stimulated emission in the fluorescent marker in the sample in a region around the excitation beam to restrict the size of the region within which the fluorescent markers are excited and wherein the depletion laser source goes through an optical element which creates a cone refractive pattern which induces stimulated emission in the fluorescent marker in the sample wherein, 3D STED is provided using a one depletion laser source by using an optical element which creates a cone refractive pattern which creates an image with lateral and axial resolution and the cone refractive pattern has a substantially ovoid shaped light intensity, with light being absent from the ovoid inner volume.

2. A STED microscope as claimed in claim 1 wherein, the optical element comprises a cone refractive crystal arrangement which creates conical refraction.

3. A STED microscope as claimed in claim 2 wherein, the optical element comprises a cone refractive crystal arrangement which creates conical refraction at the crystal with a pseudovector.

4. A STED microscope as claimed in claim 1 wherein, the optical element is a biaxial or birefringent crystal.

5. A STED microscope as claimed in claim 4 wherein, the biaxial or birefringent crystal cut in the direction which creates the conical refraction phenomenon.

6. A STED microscope as claimed in claim 4 wherein, the crystal is a rare earth crystal.

7. A STED microscope as claimed in claim 4 wherein, the cone refractive pattern is controllable by varying crystal length.

8. A STED microscope as claimed in claim 4 wherein, the cone refractive pattern is controllable by varying the crystal material.

9. A STED microscope as claimed in claim 4 wherein, the cone refractive pattern is controllable by varying the focal length of the input lens.

10. A STED microscope as claimed in claim 1 wherein, the optical element induces stimulated emission in the fluorescent marker in the sample in a 3D region surrounding one point of the excitation beam.

11. A STED microscope as claimed in claim 1 wherein, the beam created by the depletion laser source and formed using the CR crystal propagates through two or more optical elements to produce controllable hollow 3D light spot.

12. A STED microscope as claimed in claim 1 wherein, the excitation laser source and the depletion laser source operate in the visible region of the electromagnetic spectrum.

13. A STED microscope as claimed in claim 1 wherein the depletion laser source has a Gaussian intensity distribution.

14. A STED microscope as claimed in claim 1, further comprising an excitation laser source and a depletion laser source operable to create stimulated emission and depletion at multiple wavelengths.

* * * * *